(12) United States Patent
Baid

(10) Patent No.: US 9,289,579 B2
(45) Date of Patent: Mar. 22, 2016

(54) NEEDLE TIP GUARD

(75) Inventor: Rishi Baid, New Delhi (IN)

(73) Assignee: Poly Medicure Limited, Faridabad (IN)

( * ) Notice: Subject to any disclaimer, the term of this patent is extended or adjusted under 35 U.S.C. 154(b) by 932 days.

(21) Appl. No.: 13/497,700

(22) PCT Filed: May 7, 2010

(86) PCT No.: PCT/IB2010/052034
§ 371 (c)(1),
(2), (4) Date: Mar. 22, 2012

(87) PCT Pub. No.: WO2011/036574
PCT Pub. Date: Mar. 31, 2011

(65) Prior Publication Data
US 2012/0232500 A1     Sep. 13, 2012

(30) Foreign Application Priority Data

Sep. 22, 2009   (IN) .......................... 1965/DEL/2009

(51) Int. Cl.
*A61M 5/00*      (2006.01)
*A61M 25/06*    (2006.01)
*A61M 5/32*      (2006.01)

(52) U.S. Cl.
CPC .......... *A61M 25/0618* (2013.01); *A61M 5/3273* (2013.01); *A61M 25/0637* (2013.01)

(58) Field of Classification Search
CPC .................... A61M 25/0606; A61M 25/0618; A61M 25/0693; A61M 5/3273
USPC ........ 604/110, 192–198, 164.01–170.03, 263
See application file for complete search history.

(56) References Cited

U.S. PATENT DOCUMENTS

| 6,203,527 | B1 | 3/2001 | Zadini et al. |
| 7,530,965 | B2 * | 5/2009 | Villa ................... A61M 5/3273 604/110 |
| 2005/0277879 | A1 * | 12/2005 | Daga ................ A61M 25/0618 604/110 |

FOREIGN PATENT DOCUMENTS

| EP | 0352928 A1 | 1/1990 |
| EP | 0750918 A2 | 1/1997 |
| WO | 03/011381 A1 | 2/2003 |
| WO | 2005/087296 A | 9/2005 |
| WO | 2009/010847 A2 | 1/2009 |

OTHER PUBLICATIONS

International Search Report for PCT/IB2010/052034 dated Nov. 16, 2010.

* cited by examiner

*Primary Examiner* — Phillip Gray
(74) *Attorney, Agent, or Firm* — IP Attorneys Group, LLC

(57) ABSTRACT

The invention relates to a needle guard for use in a medical device, in particular for use in a catheter device, including a base portion having a needle passage extending in an axial direction from a proximal side of said base portion through said base portion to a distal side of said base portion wherein a needle shaft having a principle outer profile can be movably arranged in said needle passage; first and second arms extending substantially in said axial direction from said distal side of said base portion, wherein said first arm has a distal region and a proximal region; and a distal wall transversely arranged at said distal region of said first arm. The invention further relates to a catheter apparatus including such a needle guard and a needle.

17 Claims, 4 Drawing Sheets

Figure 1:
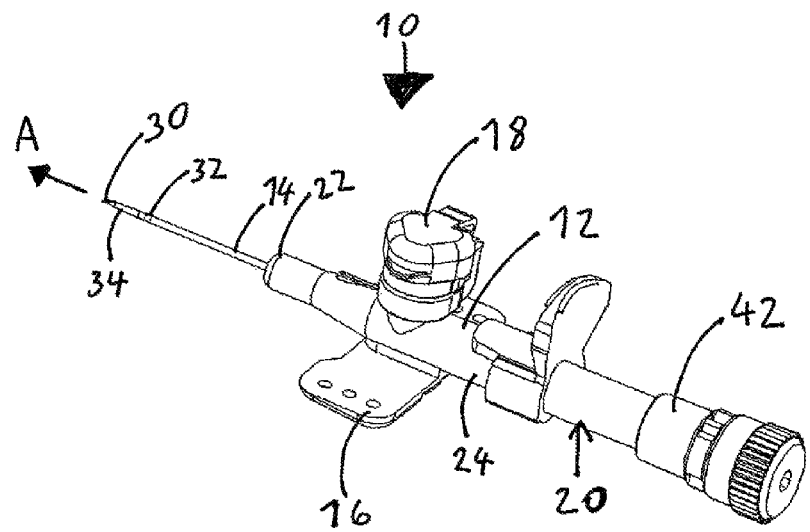

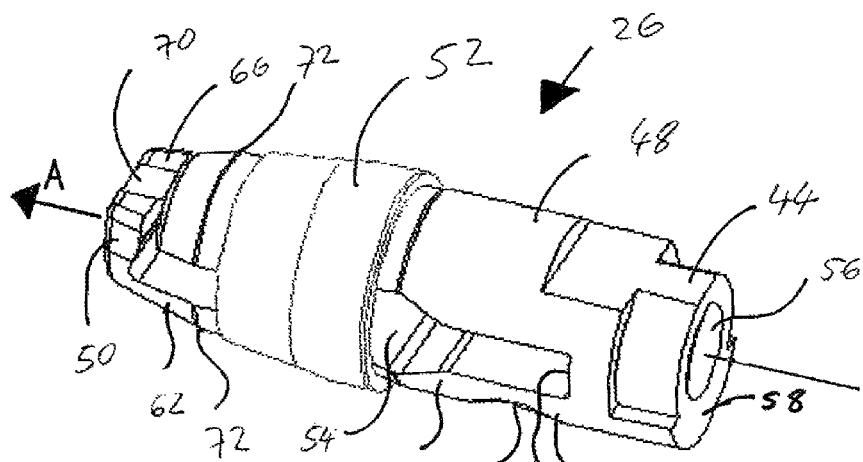
Fig. 3A
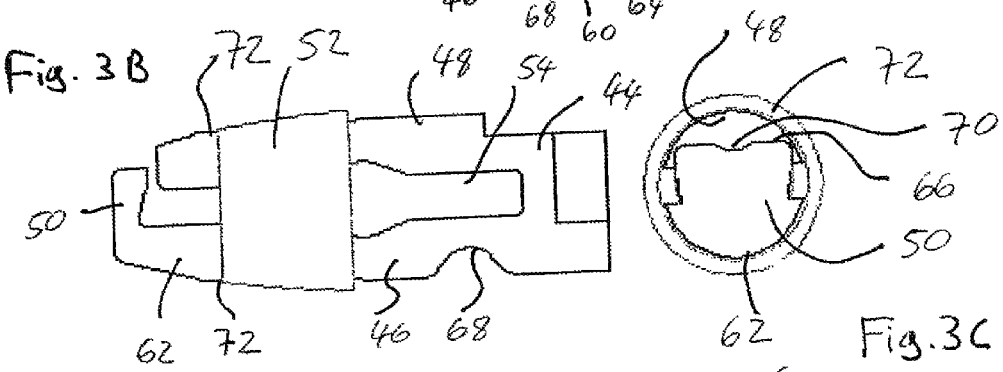
Fig. 3B
Fig. 3C
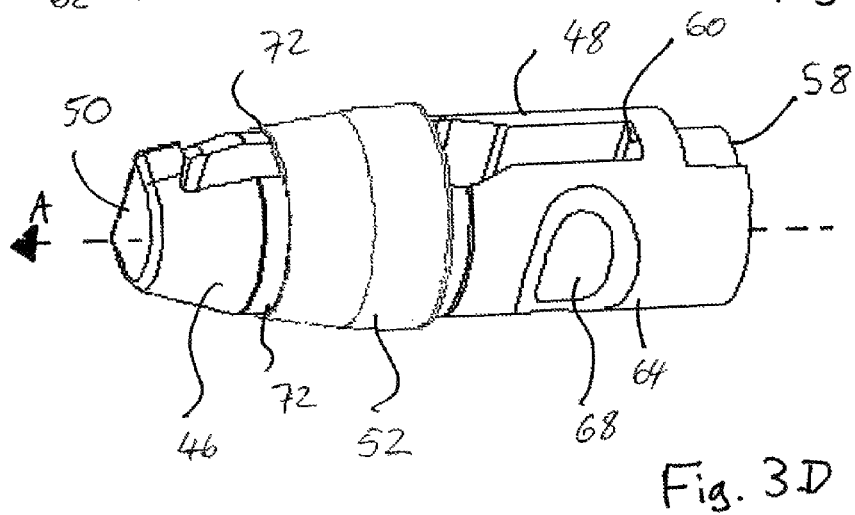
Fig. 3D

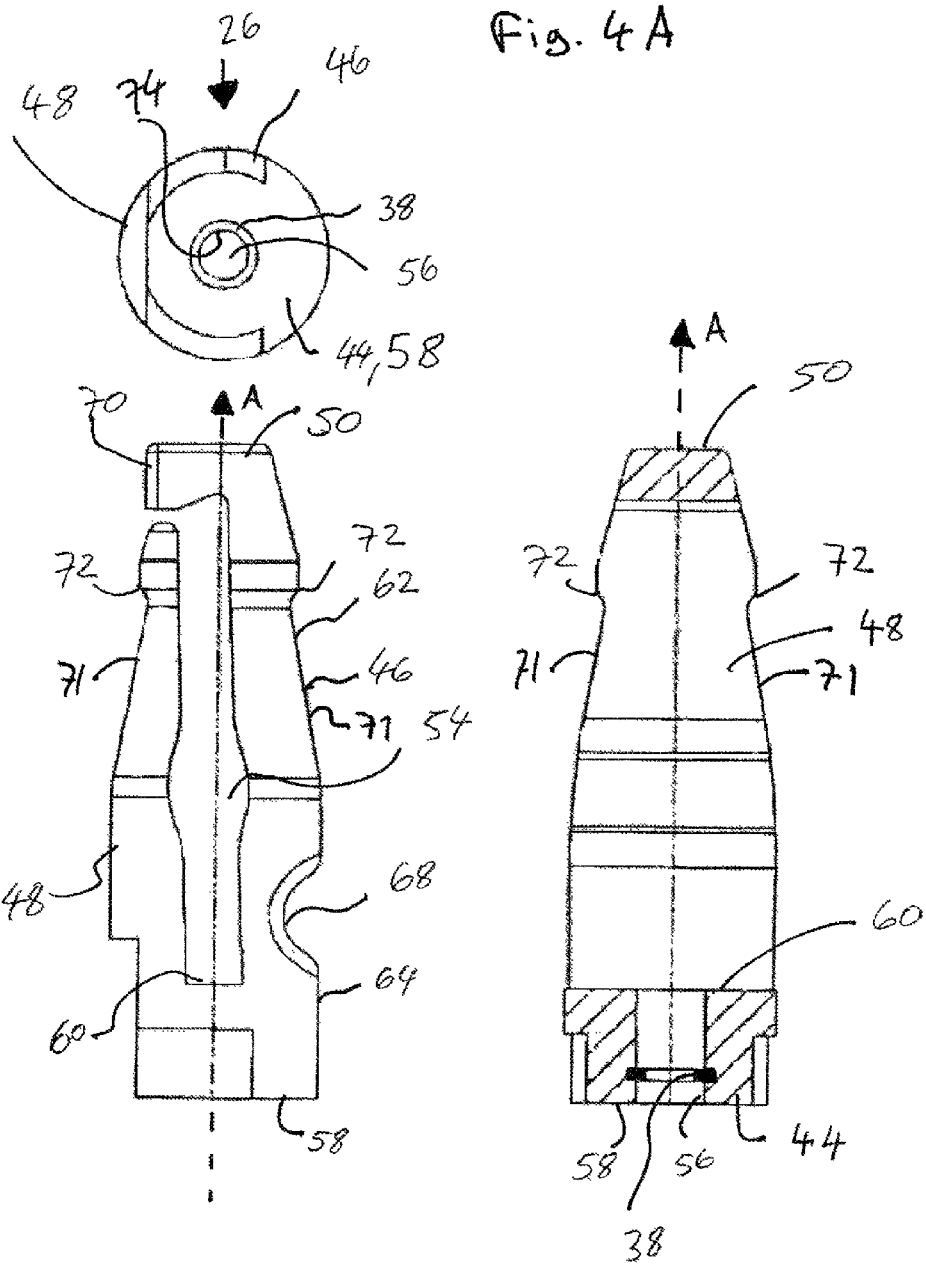

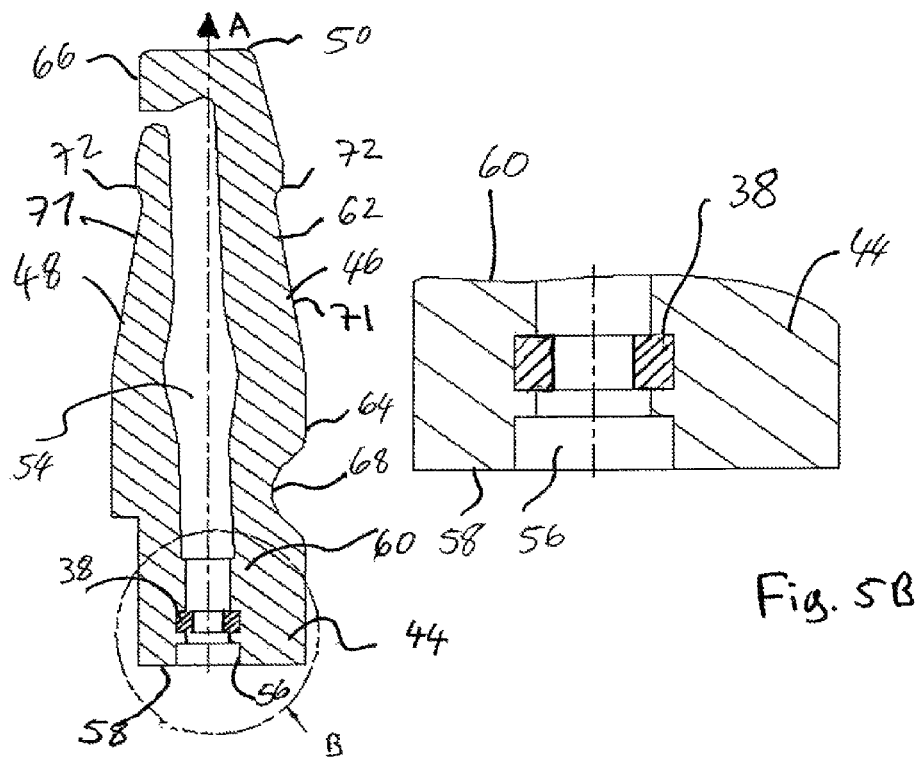
Fig. 5A
Fig. 5B
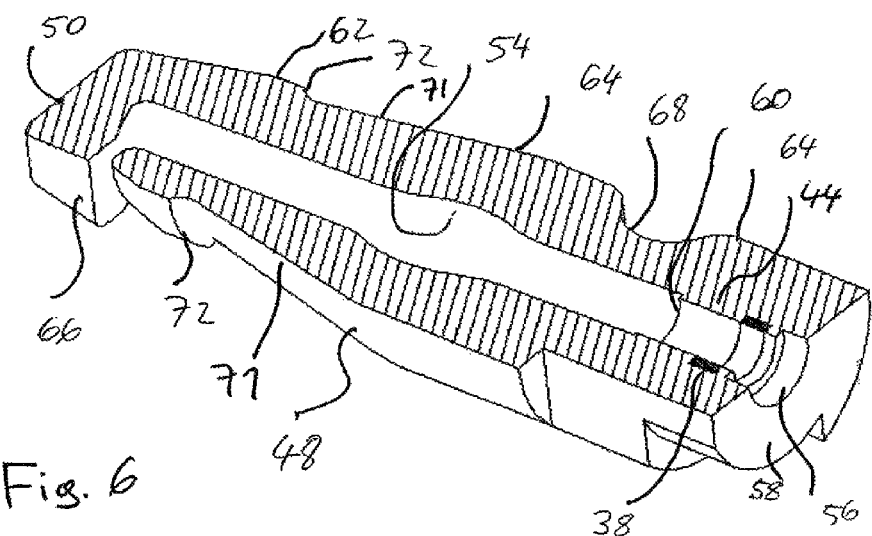
Fig. 6

NEEDLE TIP GUARD

This application is a national stage application of PCT/IB2010/052034, filed May 7, 2010, which claims priority to IN Pat. No. 1965/DEL/2009, filed Sep. 22, 2009, the entire contents and disclosures of which is hereby incorporated by reference.

The invention relates to a needle guard for use in a medical device, in particular for use in a catheter apparatus. The needle guard includes a base portion having a needle passage extending in an axial direction from a proximal side of the base portion through the base portion to a distal side of the base portion. The needle guard further includes first and second arms extending substantially in the axial direction from the distal side of the base portion and a distal wall which is transversely arranged at a distal region of the first arm.

Such needle guards are generally known and are used to cover the tip of a needle of a medical device after use of the medical device. Typically, needle guards are devised to automatically cover the needle tip after withdrawal of the needle, for example, from a patient. The needle guard thereby serves to prevent accidental pricking of, for example, a medical practitioner by the needle tip after removal of the needle from the medical device. Thereby the needle can be safely disposed of after use, without the danger of transmitting possibly highly infectious and/or deadly diseases to the medical practitioner from the patient.

Generally speaking, the term proximal refers to a region of the device or a location on the device which is closest to, for example, a clinician using the device. In contrast to this, the term distal refers to a region of the device which is farthest from the clinician, for example, the distal region of a needle will be the region of a needle containing the needle tip which is to be inserted e.g. into a patient's vein.

It is an object of the invention to provide an improved needle guard.

This object is satisfied by a needle guard in accordance with the independent claims.

According to claim 1, the needle guard of the present invention includes a base portion made of a first material and having a needle passage which extends in an axial direction from a proximal side of the base portion through the base portion to a distal side of the base portion, such that a needle having a principal outer profile can be movably arranged in the needle passage. The needle guard further includes first and second arms extending substantially in the axial direction from the distal side of the base portion, with the first arm having a distal region and a proximal region. A distal wall is transversely arranged in the distal region of the first arm.

The needle guard also includes a stopping element which is arranged in the needle guard. The stopping element is made of a second material different from the first material and has a through-bore with a profile which is adapted to the principal outer profile of the needle shaft. In the case of e.g. circular cross-sections, a diameter of the through-bore can be slightly larger than a principal outer diameter of the needle.

In order to allow a trouble free movement of the needle relative to the needle guard when the needle is withdrawn from the catheter tube, the stopping element is preferably arranged such that its through-bore is in general alignment with the needle passage of the needle guard.

The stopping element can be a circular disk, a ring, or a washer. However, it need not necessarily be circular and can have any other geometric shape such as a rectangular, square or triangular shape.

Preferably, the second material is of greater hardness and/or stiffness than the first material. For example, the first material could be a plastic material and the second material could consist of a metal, a ceramic or a rubber material, or any other type of material which is stiff and not as easily distorted as the first material.

Needle guards of the above kind are used, for example, in catheter apparatuses. The invention therefore also provides a catheter apparatus including a needle guard in accordance with the present invention, with the catheter apparatus further including a catheter tube, a catheter hub and a needle having a needle shaft, a needle tip and a needle hub, wherein the needle shaft has a distal section and a proximal section, with at least the proximal section having a principal outer profile.

The needle also has an enlargement provided between the distal section and the proximal section of the needle shaft. The enlargement has an outer profile one dimension of which is larger than a maximum dimension of the profile of the through-bore of the stopping element. In a preferred embodiment, the enlargement is made by a crimping of the needle shaft. However, other ways of forming the enlargement are possible, such as applying additional material to the needle shaft, e.g. by soldering, welding or gluing etc.

The inner profile of the needle can either be reduced in the region of the enlargement, for example, if the enlargement is formed by crimping, or it can be substantially constant throughout the length of the needle, for example, if the enlargement is formed by applying additional material to the needle shaft.

Prior to the use of the catheter apparatus, the needle guard is arranged in the catheter hub near a proximal end of the needle shaft. In this situation, the needle extends completely through the needle guard, thereby deflecting the first arm of the needle guard outwards, i.e. at an angle to the axial direction, such that the distal wall of the first arm is supported on the needle shaft. Following the insertion of the catheter into a patient, the needle is withdrawn from the catheter tube and the needle shaft moves through the needle guard while the needle guard is retained in the catheter hub. Once the needle tip passes the transverse distal wall of the needle guard, i.e. such that the needle shaft no longer supports the distal wall, a restoring force ensures that the first arm of the needle guard is moved back into alignment with the axial direction of the needle guard, so that the needle tip is blocked by the distal wall of the needle guard, i.e. the needle tip is prevented from axially projecting out of the needle guard.

Once the needle tip is blocked by the distal wall, the enlargement of the needle shaft engages with the stopping element to prevent the needle guard from being removed from the needle shaft. The fact that the stopping element is made from a second material which is harder and less easily distorted than the first material of the base portion, has the effect that the needle guard is secured more effectively on the needle shaft and can be retained even if excessive external force is applied when pulling on the needle, as the enlargement is prevented from being pulled through the base portion of the needle guard due to the stopping element. Hence, it is less likely that the needle guard is removed from the needle tip accidentally and, as a result, the needle guard provides a better protection against accidental pricking and thus increased safety for the person handling the catheter apparatus.

In a further embodiment of the needle guard, a tension element surrounds the first and second arms of the needle guard. In the deflected state of the first arm, the tension element is expanded against a restoring force of the tension element. Once the needle shaft no longer supports the distal wall, the tension element aids the repositioning of the first arm back into axial alignment with the axial direction. This repositioning is necessary so that the distal wall can block the needle tip from axially sliding out of the needle guard. In addition, the tension element helps to enclose a space between the first and second arms and thus helps to prevent the needle tip from projecting sideways out of the needle guard. In other words, the tension element adds to the protective effect of the needle guard.

In a further embodiment of the needle guard, a recess is provided in the proximal region of the first arm of the needle guard. This recess increases the deflectability of the first arm in the region it is provided and thereby reduces the restoring force acting on the distal wall while this is being supported by the needle shaft. This allows the needle shaft to be moved more easily relative to the distal wall, as the frictional force acting on the needle shaft is reduced.

In a further embodiment of the needle guard, a groove is provided in a side of the distal wall, with the groove extending substantially in the axial direction. The groove acts as a guide groove for the needle shaft and aids the axial movement of the needle shaft relative to the needle guard. Moreover, the needle shaft is prevented from sliding sideways off the distal wall. Such a sideways movement would significantly increase the force required to move the needle shaft relative to the needle guard, which would prevent a correct functioning of the needle guard.

Further subject matter of the present invention satisfying the above mentioned object includes a needle guard according to claim 4 and a needle guard according to claim 7. In particular, such needle guards do not include stopping elements. Thus, the needle guard of the present invention can also be adapted such that it includes a recess and/or a groove as discussed above, but without including the stopping element. In this case, the outer profile of the enlargement of the needle shaft must be greater than the profile of the throughbore in the base portion of the needle guard, in order to prevent the needle guard from sliding off the needle in a distal direction.

Further advantageous embodiments of the invention and preferred apparatuses for carrying out the invention are set forth in the subordinate claims and are described in connection with the accompanying drawings.

Figure 2:
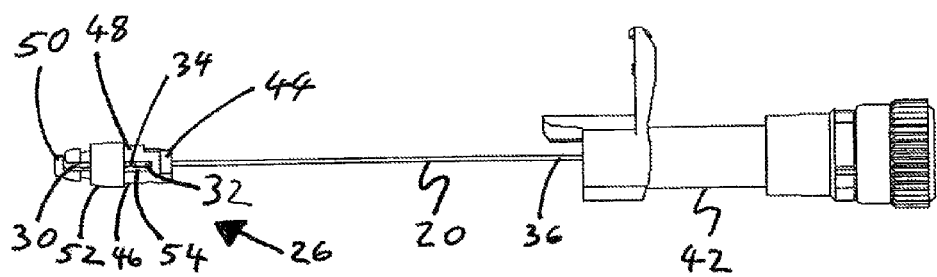

The present invention will now be explained in more detail in the following with reference to preferred embodiments and to the accompanying drawings in which are shown:

FIG. 1 a catheter apparatus in accordance with the present invention;

FIG. 2 a needle, needle hub and needle guard removed from the catheter apparatus of FIG. 1;

FIG. 3A-3D the needle guard of FIG. 2;

FIG. 4A-4C further illustrations of the needle guard of FIG. 2 without a tension element;

FIG. 5A-5B sectional illustrations of the needle guard of FIG. 4; and

FIG. 6 a partially sectional and partially perspective illustration of the needle guard of FIG. 4.

FIG. 1 shows a catheter apparatus 10 in accordance with the invention. The catheter apparatus 10 includes a catheter hub 12, a catheter tube 14, wings 16, a port 18 and a needle 20. The catheter hub 12 has a distal end 22 and a proximal end 24, the catheter tube 14 is arranged adjacent to the distal end 22 of the catheter hub 12.

The needle 20, shown in FIG. 2, has a needle shaft 28, a needle tip 30 at a distal section 34 of the needle shaft and a needle hub 36 attached to a proximal end 36 of the needle shaft 28. Both, the distal section 34 and the proximal section 36 generally have the same outer profile. In the present embodiment, the distal and proximal sections 34, 36 have circular cross-sections with generally identical outer diameters.

An enlargement 32 of the needle 20 is provided between the distal section 34 and the proximal section 36 of the needle shaft 28. The enlargement 32 has a maximum dimension in a direction transverse to the needle shaft 28, which is greater than the outer diameter of the distal and proximal sections 34, 36. The enlargement 32 can be made, for example, by crimping the needle shaft 28.

Prior to use of the catheter apparatus 10, the needle 20 is received in the catheter hub 12 and catheter tube 14, such that the needle shaft 28 extends through the length of the catheter tube 14.

A needle guard 26 is movably arranged on the needle shaft 28 and retained in the catheter hub 12 prior to use of the catheter apparatus 10. The needle guard 26 has a base portion 44, a first arm 46, a second arm 48 and a distal wall 50. The distal wall 50 is arranged at a distal end of the first arm 46 and extends in a direction transverse to an axial direction A. A tension element 52, for example, a rubber band or the like, surrounds the first and second arms 46, 48.

Upon withdrawal of the needle 20 from the catheter tube 14 and catheter hub 12 the needle shaft 28 moves relative to the needle guard 26 until the needle tip 30 is received in the needle guard 26. Once the needle tip 30 is received in the needle guard 26 the enlargement 32 of the needle shaft 28 engages with the base portion 44 of the needle guard 26 such that the needle guard 26 can be pulled out of the catheter hub 12 together with the needle 20. An axial movement of the needle 20 relative to the needle guard 26 is now limited, as the distal wall 50 blocks the needle tip 30 and the engagement between the enlargement 32 and the base portion 44 of the needle guard 26 prevents the needle tip from being removed via the base portion 44, i.e. the needle tip 30 is safely surrounded by the needle guard 26, as is shown in FIG. 2.

FIGS. 3 to 6 show the needle guard 26 in more detail.

As can be seen from FIG. 3A, the base portion 44 has a needle passage 56 extending in the axial direction A from a proximal side 58 of the base portion 44 through the base portion 44 to a distal side 60 of the base portion 44. The needle passage 56 is configured to receive the proximal section 36 of the needle shaft 28 and allow movement of the needle shaft 28 relative to the needle guard 26. For this reason, the diameter of the needle passage 56 is slightly larger than the outer diameter of the proximal section 36 of the needle shaft 28.

The first and second arms 46, 48 of the needle guard 26 extend generally in the axial direction A from the distal side 60 of the base portion 44, i.e. generally parallel to the needle shaft 28. The first arm 46 has a distal region 62 and a proximal region 64, with a recess 68 being provided in the proximal region 64 of the first arm 46. The recess 68 is provided to facilitate deflection of the first arm 46 and to reduce a restoring force acting on the first arm 46 when the first arm 46 is deflected off axis.

The outer surfaces 71 of the distal regions 62 of the first and second arms 46, 48 generally taper from the base portion 44 towards the distal wall 50. At their distal ends, the tapered surfaces 71 are limited by protrusions or shoulders 72 formed on the first and second arms 46, 48. The shoulders 72 and the tapered surfaces 71 define the axial position of the tension element 52 and, in particular, prevent the tension element 52 from axially sliding off the first and second arms 46, 48.

The transverse distal wall 50 has a side 66 at its free end, in which a groove 70 is provided. The groove 70 extends in a direction generally parallel to the axial direction A and is used to guide the needle shaft 28.

As mentioned above, prior to the use of the catheter apparatus 10 the needle 20 extends through the catheter tube 14 and the needle guard 26 is arranged in the catheter hub 12. In this situation, the distal wall 50 of the needle guard 26 contacts the needle 20, with the needle shaft 28 being guided in the groove 70 in the side 66 of the distal wall 50. The needle shaft 28 thereby supports the distal wall 50, due to which the first arm 46 of the needle guard 26 is deflected outwards, i.e. away from the needle 20, against a restoring force of the tension element 52.

In order to retain the needle guard 26 in the catheter hub 12 while the needle 20 is being withdrawn from the catheter tube 14, the shoulders 72 provided on both the first arm 46 and the second arm 48 of the needle guard 26 engage with recesses or protrusions or combinations thereof (not shown) provided in the catheter hub 12. The protrusions may form an annular ring extending along the entire inner periphery of the catheter hub 12, or they may form one or more ring segments extending along only a respective part of the inner periphery of the catheter hub 12. Similarly, the recesses may form an annular groove extending along the entire inner periphery of the catheter hub 12, or they may form one or more groove segments extending along only a respective part of the inner periphery of the catheter hub 12.

Once the needle 20 has been withdrawn such that the needle tip 30 has passed the distal wall 50 and is received between the first and second arms, the needle shaft 28 no longer supports the distal wall 50. This causes the first arm 46 to reposition itself in axial alignment with the needle 20 due to the restoring force acting on the first arm 46 in its deflected state. The realignment of the first arm 46 is aided through the use of the tension element 52. The realignment of the first arm 46 causes the shoulders 72 to disengage from the recesses or protrusions in the catheter hub 12 allowing the needle guard 26 covering the needle tip 30 to be removed from the catheter hub 12 together with the needle 20, with the guarded needle tip 30 being arranged in a space 54 which is bounded by the base portion 44, the first and second arms 46, 48, the distal wall 50 and the tension element 52.

A stopping element 38 is provided in the needle guard 26. According to the present embodiment, the stopping element 38 is arranged in the base portion 44 of the needle guard 26 (see FIG. 4A and FIG. 4C). However, it is to be understood that the stopping element 38 need not be arranged in the base portion 44 itself, but can also be arranged at the distal side 60 thereof between the first arm 46 and the second arm 48. The position of the stopping element 38 in the base portion 44 can be selected freely.

Moreover, the stopping element 38 need not be arranged perpendicular to the longitudinal axis A, but can be arranged at an angle relative to the longitudinal axis A, e.g. so that the through hole of the stopping element 38 is aligned with the groove 70 of the distal wall 50, when the first arm 46 is deflected. The angle the stopping element 38 is placed at inside the base portion 44 relative to the longitudinal axis A can be selected in the range between 55° and 85° to the longitudinal axis A, preferably at an angle in the range between 60° and 80° to the longitudinal axis A. Placing the stopping element at an angle to the longitudinal axis A allows a reduction of the frictional force acting on the needle while the needle is being withdrawn.

The stopping element 38 has a disk-like shape, similar to a washer, and is made of a material different to the material of the base portion 44, in particular, a material having a greater hardness and/or stiffness than the material of the base portion 44. Preferably, the stopping element 38 is made of metal or ceramic, but it can be made out of any other material which is stiff and is not easily bent.

The base portion 44 and first and second arms 46, 48 of the needle guard 26 can be made from a plastic material, for example by a moulding process, with the stopping element 38 placed within the mould prior to the moulding process. The material of the base portion 44 and the first and second arms 46, 48 is different to the material of the stopping element 38.

The stopping element 38 has a through-bore 74 which has a circular cross-section with its diameter being slightly larger than the principle diameter of the proximal section 36 of the needle shaft 28, in order to allow movement of the proximal section 36 of the needle shaft 28 relative to the stopping element 38. At the same time the diameter of the through-bore 74 is not only smaller than that of the needle passage 56 but also smaller than the maximum dimension of the enlargement 32 of the needle shaft 28, in order to prevent the enlargement 32 from passing through the through-bore 74.

Even in the event that an excessive external force is applied to the needle 20 and/or the needle guard 26, the stopping element 38 prevents the enlargement 32 of the needle shaft from being pulled through the needle passage 56 of the base portion 44. Thus, the stopping element 38 improves the safety of the needle guard 26.

LIST OF REFERENCE NUMERALS 10 catheter
12 catheter hub
14 catheter tube
16 wings
18 port
20 needle
22 distal end
24 proximal end
26 needle guard
28 needle shaft
30 needle tip
32 enlargement
34 distal section
36 proximal section
38 stopping element
42 needle hub
44 base portion
46 first arm
48 second arm
50 distal wall
52 tension element
54 space
56 needle passage
58 proximal side
60 distal side
62 distal region
64 proximal region
66 side
68 recess
70 groove
71 outer surface
72 shoulder
74 through-bore
A axial direction
B detail

What is claimed is:
1. A needle guard (26) for use in a medical device, in particular for use in a catheter device (10), including;

a base portion (44) made of a first material and having a needle passage (56) extending in an axial direction (A) from a proximal side (58) of said base portion (44) through said base portion (44) to a distal side (60) of said base portion (44), wherein a needle shaft (28) having a principal outer profile can be movably arranged in said needle passage (56);

first and second arms (46,48) extending substantially in said axial direction (A) from said distal side (60) of said base portion (44), wherein said first arm (46) has a distal region (62) and a proximal region (64); and said first arm (46) includes a distal wall (50) transversely arranged at said distal region (62) of said first arm (46); wherein said distal wall (50) includes a side (66); said side (66) includes a groove (70); said groove (70) extending substantially in said axial direction (A); and said groove (70) includes a notch for receiving the needle shaft (28).

2. A needle guard (26) in accordance with claim 1, wherein a recess (68) is provided in said proximal region (64) of said first arm (46).

3. A needle guard (26) in accordance with claim 1, wherein a stopping element (38) is arranged in said needle guard (26), said stopping element (38) being made of a second material different from said first material and having a through-bore (74) with a profile that is adapted to the principal outer profile of the needle shaft (28).

4. A catheter apparatus (40), including:
a catheter tube (14);
a catheter hub (12);
a needle (20) having a needle tip (30), a needle shaft (28) and a needle hub (42), wherein said needle shaft (28) has a distal section (34) and a proximal section (36), with at least the proximal section (36) having a principal outer profile;
wherein said needle shaft (28) has an enlargement (32) between said distal section (34) and said proximal section (36), said enlargement (32) having an increased outer profile a dimension of which is larger than a maximum dimension of a profile of a needle passage (56) and a stopping element (38);
wherein said stopping element (38) includes an angle between approximately 55° and approximately 85° relative to a longitudinal axis.

5. A needle guard (26) in accordance with claim 3, wherein said stopping element (38) is arranged such that its through-bore (74) is in general alignment with said needle passage (56) in said needle guard (26).

6. A needle guard (26) in accordance with claim 3, wherein said stopping element (38) is arranged in said base portion (44).

7. A needle guard (26) in accordance with claim 3, wherein said stopping element (38) has a disk-like shape and/or is made as a ring or as a washer.

8. A needle guard (26) in accordance with claim 3, wherein said second material is of a greater hardness and/or stiffness than the first material.

9. A needle guard (26) for use in a medical device, in particular for use in a catheter device (10), including:
a base portion (44) made of a first material and having a needle passage (56) extending in an axial direction (A) from a proximal side (58) of said base portion (44) through said base portion (44) to a distal side (60) of said base portion (44) for movably receiving a needle shaft (28) having a principle outer profile;
first and second arms (46, 48) extending substantially in said axial direction (A) from said distal side (60) of said base portion (44), wherein said first arm (46) has a distal region (62) and a proximal region (64);
a stopping element (38) made of a second material different from said first material, which is arranged in said needle guard (26) and has a through-bore (74) with a profile that is adapted to the principal outer profile of the needle shaft (28);
wherein said stopping element (38) includes an angle between approximately 55° and approximately 85° relative to a longitudinal axis;
wherein a recess (68) is provided in said proximal region (64) of said first arm (46); and
wherein said first arm (46) includes a distal wall (50) transversely arranged at said distal region (62) of said first arm (46); wherein said distal wall (50) includes a side (66); said side (66) includes a groove (70); said groove (70) extending substantially in said axial direction (A); and said groove (70) includes a notch for receiving the needle shaft (28).

10. A needle guard (26) in accordance with claim 9, wherein said stopping element (38) is arranged such that its through-bore (74) is in general alignment with said needle passage (56) in said needle guard (26).

11. A needle guard (26) in accordance with claim 9, wherein said stopping element (38) is arranged in said base portion (44).

12. A needle guard (26) in accordance with claim 9, wherein said stopping element (38) has a disk-like shape and/or is made as a ring or as a washer.

13. A needle guard (26) in accordance with claim 9, wherein said second material is of a greater hardness and/or stiffness than the first material.

14. A needle guard (26) in accordance with claim 9, wherein a tension element (52) is provided which is arranged such that said tension element (52) surrounds said first and second arms (46, 48) of said needle guard (26).

15. A needle guard (26) for use in a medical device, in particular for use in a catheter device (10), including:
a base portion (44) made of a first material and having a needle passage (56) extending in an axial direction (A) from a proximal side (58) of said base portion (44) through said base portion (44) to a distal side (60) of said base portion (44), wherein a needle shaft (28) having a principal outer profile can be movably arranged in said needle passage (56);
first and second arms (46,48) extending substantially in said axial direction (A) from said distal side (60) of said base portion (44), wherein said first arm (46) has a distal region (62) and a proximal region (64), and wherein a recess (68) is provided in said proximal region (64) of said first arm (46);
said first arm (46) includes a distal wall (50) transversely arranged at said distal region (62) of said first arm (46); wherein said distal wall (50) includes a side (66); said side (66) includes a groove (70); said groove (70) extending substantially in said axial direction (A); and said groove (70) includes a notch for receiving the needle shaft (28).

16. A needle guard (26) in accordance with claim 15, wherein a stopping element (38) is arranged in said needle guard (26), said stopping element (38) being made of a second material different from said first material and having a through-bore (74) with a profile that is adapted to the principal outer profile of the needle shaft (28).

17. A needle guard (26) in accordance with claim 15, wherein said stopping element (38) is arranged in said base portion (44).

\* \* \* \* \*